US00PP26709P3

(12) United States Plant Patent
Larson et al.

(10) Patent No.: US PP26,709 P3
(45) Date of Patent: May 10, 2016

(54) STRAWBERRY PLANT NAMED 'FRONTERAS'

(50) Latin Name: ***Fragaria×ananassa* Duch.**
Varietal Denomination: Fronteras

(71) Applicant: The Regents of the University of California, Oakland, CA (US)

(72) Inventors: Kirk D. Larson, Santa Ana, CA (US); Douglas V. Shaw, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 67 days.

(21) Appl. No.: 13/999,312

(22) Filed: Feb. 10, 2014

(65) Prior Publication Data

US 2015/0230374 P1 Aug. 13, 2015

(51) Int. Cl.
*A01H 5/08* (2006.01)

(52) U.S. Cl.
USPC ..... Plt./208

(58) Field of Classification Search
USPC ..... Plt./208, 209
CPC ..... A01H 5/0893; A01H 5/08
See application file for complete search history.

(56) References Cited

PUBLICATIONS http://www.darensberries.com/our-berries/; 2013; 1 page.*

* cited by examiner

*Primary Examiner* — Kent L Bell
(74) *Attorney, Agent, or Firm* — Kilpatrick Townsend & Stockton LLP

(57) ABSTRACT

'Fronteras' is a short-day (June bearing) cultivar similar to 'Camarosa' (U.S. Plant Pat. No. 8,708), but with greater productivity, higher quality fruit, and earlier production; it is similar to 'Ventana' (U.S. Plant Pat. No. 13,469) and 'Benicia' (U.S. Plant Pat. No. 22,542), but with somewhat later production, a larger plant, larger fruit size, and higher quality fruit.

3 Drawing Sheets

Genus and species: The strawberry cultivar of this invention is botanically identified as *Fragaria×ananassa* Duch.

Variety denomination: The variety denomination is 'Fronteras'.

BACKGROUND OF THE INVENTION

This invention relates to a new and distinctive short-day type cultivar designated as 'Fronteras', which resulted from a cross performed in 2008 between two unreleased germplasm accessions Cal 4.18-4 and Cal 5.165-1. Accession Cal 4.18-4 was chosen as a parent due to its very high early productivity, large and high quality fruit, and moderate plant vigor. Accession Cal 5.165-1 was chosen as a parent due to its vigorous but open plant habit and firm, large and flavorful fruit, and extended productivity.

'Fronteras' was first fruited near Irvine, Calif. in 2009, where it was selected, originally designated Cal 8.132-608, and propagated asexually by runners. Following selection and during testing the plant of this selection was designated 'C235'. With the decision that this plant was to be released, this plant was given the name 'Fronteras' for purposes of introduction into commerce and for international registration and recognition. Asexual propagules from this original source have been tested in Watsonville Calif. and near Irvine, Calif., and to a limited extent in grower fields starting in 2010. The cultivar is stable and reproduces true to type in successive generations of asexual reproduction.

BRIEF SUMMARY OF THE INVENTION

'Fronteras' is a short-day (June bearing) cultivar similar to 'Camarosa' (U.S. Plant Pat. No. 8,708), but with greater productivity, higher quality fruit, and earlier production; it is similar to 'Ventana' (U.S. Plant Pat. No. 13,469) and 'Benicia' (U.S. Plant Pat. No. 22,542), but with somewhat later production, a larger plant, larger fruit size, and higher quality fruit.

BRIEF DESCRIPTION OF THE DRAWINGS

The Figures depict various characteristics of the 'Fronteras' cultivar.

DETAILED DESCRIPTION OF THE INVENTION

Figure 1:
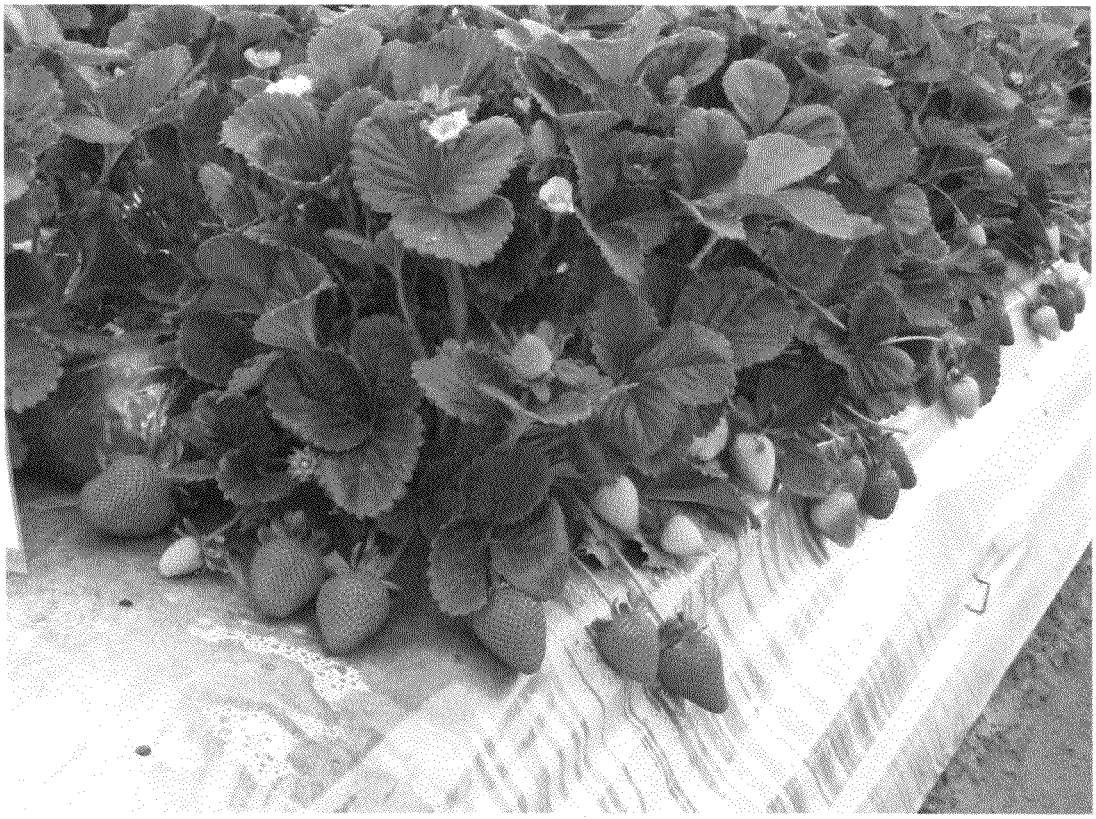
FIG. 1 shows the general flowering and fruiting characteristics of the plant in a field planting.
Figure 2:
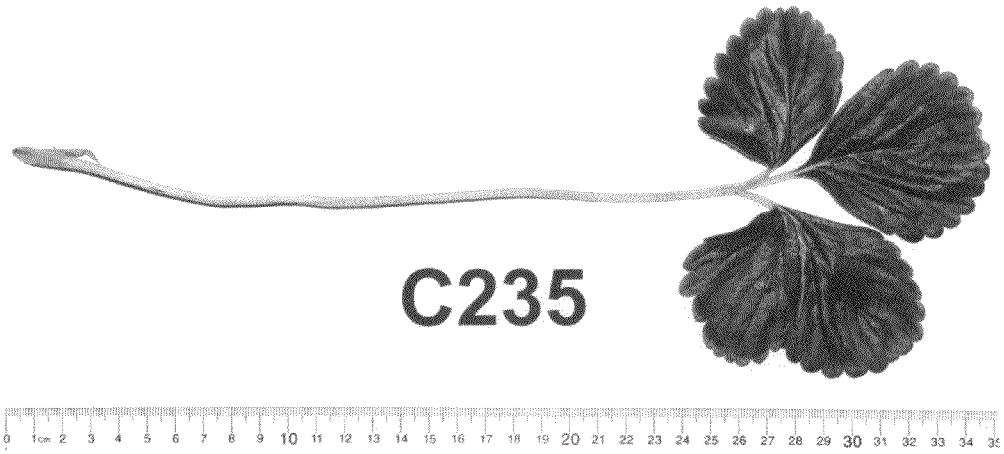
FIG. 2 shows a typical leaf at mid-season.
Figure 3:
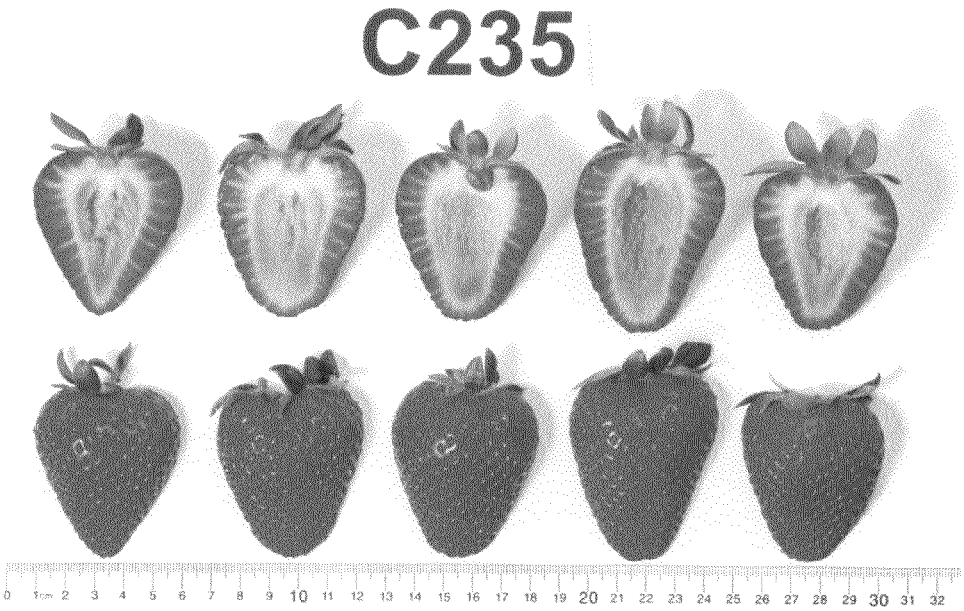
FIG. 3 shows representative mid-season fruit.

'Fronteras' is typical of short-day strawberry cultivars and produces fruit over an extended period when treated appropriately in arid, subtropical climates. The production pattern for 'Fronteras' is similar to that for 'Camarosa' (U.S. Plant Pat. No. 8,708), although it is slightly earlier to initiate fruiting with most cultural treatments. 'Fronteras' initiates fruiting slightly later than 'Ventana' (U.S. Plant Pat. No. 13,469) and 'Benicia' (U.S. Plant Pat. No. 22,542) when established in very early fall. Fruit from Fronteras is larger and darker than fruit from unreleased parent variety Cal 4.18-4. Fruit from Fronteras is larger, more evenly colored, and more conical than fruit from unreleased parent variety Cal 5.165-1. The plant for Fronteras is much larger than for either parent, and Fronteras produces fruit earlier in the season than Cal 5.165-

1. 'Fronteras' will be of special interest for winter plantings, where 'Camarosa', 'Ventana', and 'Benicia' have been successful, and in summer plantings where 'Chandler' (U.S. Plant Pat. No. 5,262) and 'Camino Real' (U.S. Plant Pat. No. 13,079) have been successful.

Plants and Foliage:

Fruiting plants of 'Fronteras' are slightly taller, more erect, and more open than all of the comparison cultivars in most production environments. Comparative statistics for foliar characters near mid-season are given for 'Fronteras' and three comparison cultivars in Table 1. Individual leaflets for 'Fronteras' are to those of the comparison cultivars, and are more elongated than for 'Benicia'. The leaflet base is obtuse and the leaflet margin is serrate to crenate. Leaves (including petioles) for 'Fronteras' are slightly longer than for 'Ventana' and 'Camarosa', shorter than for 'Benicia'. Petioles for 'Fronteras' are generally longer than those of 'Ventana', 'Benicia' and 'Camarosa'. The adaxial (upper) and abaxial (lower) surfaces of leaves for 'Fronteras' are lighter than for 'Camarosa' and 'Benicia', darker and less yellow than for 'Ventana' leaves at midseason. Leaves of 'Fronteras' have similar concavity to 'Camarosa', and are less concave those for 'Ventana'. Serrations at midseason are less pointed than for 'Ventana', similar in shape and number to 'Benicia' and 'Camarosa'. The stipule length is somewhat longer for 'Fronteras' than for the comparison cultivars.

TABLE 1

Foliar and plant characteristics for 'Fronteras', 'Camarosa', 'Ventana', and 'Benicia'.

| | Cultivar | | | |
|---|---|---|---|---|
| Foliar Character | 'Camarosa' | 'Ventana' | 'Benicia' | 'Fronteras' |
| Plant height (mm) | | | | |
| mean | 227 | 277 | 245 | 313 |
| range | 190-320 | 250-300 | 220-260 | 300-330 |
| Plant spread (mm) | | | | |
| mean | 368 | 425 | 414 | 421 |
| range | 300-465 | 375-525 | 360-500 | 345-485 |
| Mid-tier leaflet Length (mm) | | | | |
| mean | 85 | 89 | 80 | 83 |
| range | 70-95 | 80-110 | 70-90 | 80-90 |
| Width (mm) | | | | |
| mean | 79 | 77 | 80 | 73 |
| range | 65-90 | 70-90 | 75-80 | 60-90 |
| Mid-tier leaf Length (mm) | | | | |
| mean | 230 | 231 | 264 | 247 |
| range | 200-290 | 180-260 | 220-310 | 200-280 |
| Width (mm) | | | | |
| mean | 143 | 153 | 161 | 141 |
| range | 120-170 | 140-160 | 150-180 | 120-160 |
| Leaf components Petiole length (mm) | | | | |
| mean | 110 | 113 | 136 | 141 |
| range | 90-150 | 80-120 | 110-160 | 110-160 |
| Petiole diameter (mm) | | | | |
| mean | 3.6 | 5.3 | 4.9 | 4.6 |
| range | 3-4 | 4-7 | 4-6 | 4-5 |

TABLE 1-continued

Foliar and plant characteristics for 'Fronteras', 'Camarosa', 'Ventana', and 'Benicia'.

| | Cultivar | | | |
|---|---|---|---|---|
| Foliar Character | 'Camarosa' | 'Ventana' | 'Benicia' | 'Fronteras' |
| Petiolule length (mm) | | | | |
| mean | 5.1 | 6.9 | 5.3 | 5.7 |
| range | 4-6 | 6-8 | 4-6 | 4-7 |
| # leaflets/leaf | 3 | 3 | 3, rarely 4 or 5 | 3 |
| Leaf convexity | most flat to slight concave | flat to very concave | flat to concave | flat to concave |
| Serrations | | | | |
| number/leaf | 20.8 | 20.6 | 20.5 | 20.1 |
| range | 19-23 | 18-25 | 18-23 | 18-22 |
| shape | semi-pointed | semi-pointed | round to semi-pointed | round to semi-pointed |
| Leaf pubescence | light-moderate | moderate-heavy | moderate-light | moderate |
| Petiole pubescence | | | | |
| density | heavy | moderate-heavy | heavy | moderate-heavy |
| direction | perpendicular to acropetal | perpendicular | perpendicular to acropetal | perpendicular |
| Petiole color (Munsell) | 2.5 GY 8/9 | 7.5 GY 9/4 | 7.5 GY 8/10 | 2.5 GY 7/10 |
| Stipule length (mm) | | | | |
| mean | 27.2 | 24.0 | 31.1 | 37.5 |
| range | 20-34 | 20-30 | 25-40 | 30-40 |
| Stipule color (Munsell) | | | | |
| core | 2.5 Y 6/8 | 2.5 GY 8/9 | 2.5 Y 9/4 | 7.5 GY 8/7 |
| margins | 7.5 Y 6/7 | 5 GY 8/8 | 5 GY 8/8 | 5 GY 8/8 |
| Stolon base diameter (mm) | 11.7 | 15.2 | 16.5 | 13.2 |
| Stolons per nursery mother plant | 22.7 | 18.8 | 22.9 | 23.0 |
| Venation pattern | pinnate | pinnate | pinnate | pinnate |
| color (Munsell) | 7.5 GY 8/7 | 7.5 GY 9/4 | 7.5 GY 8/7 | 2.5 GY 9/8 |

Disease and Pest Reaction:

'Fronteras' is moderately resistant to powdery mildew (*Sphaerotheca macularis*), moderately susceptible to Anthracnose crown rot (*Colletotrichum acutatum*), and moderately resistant to *Verticillium* wilt (*Verticillium dahliae*), *Phytophthora* crown rot (*Phytophthora cactorum*) and common leaf spot (*Ramularia tulasnei*) (Table 2). When treated properly, it has tolerance to two-spotted spider mites (*Tetranychus urticae*) equal to that for the comparison cultivars. 'Fronteras' is tolerant to strawberry viruses encountered in California.

TABLE 2

Disease resistance scores for 'Fronteras' and three comparison cultivars; all scores were obtained in evaluations conducted in 2012-2013.

| Genotype | *Phytophthora* Resistance Score (5 = best) | *Verticillium* Resistance Score (5 = best) | *Colletotrichum* Resistance Score (5 = best) |
|---|---|---|---|
| 'Camarosa' | 3.6 | 2.8 | 7.3 |
| 'Ventana' | 2.1 | 2.9 | 3.0 |

TABLE 2-continued

Disease resistance scores for 'Fronteras' and three comparison cultivars; all scores were obtained in evaluations conducted in 2012-2013.

| Genotype | *Phytophthora* Resistance Score (5 = best) | *Verticillium* Resistance Score (5 = best) | *Colletotrichum* Resistance Score (5 = best) |
|---|---|---|---|
| 'Benicia' | 3.5 | 1.6 | 2.5 |
| 'Fronteras' | 4.1 | 3.7 | 2.5 |

Flowering, Fruiting, Fruit, and Production Characteristics:

'Fronteras' is similar to other California short-day strawberry cultivars (e. g. 'Ventana', 'Camarosa', and 'Benicia') in that it will flower over an extended period and into spring or summer, given appropriate local temperature and horticultural conditions. With most planting treatments 'Fronteras' produces fruit slightly later than 'Ventana' and 'Benicia' and earlier than for 'Camarosa'. Comparative statistics for flower and fruit characters near mid-season are given for the four cultivars in Table 4. The primary flowers for 'Fronteras' are slightly larger than for 'Camarosa' but smaller than 'Ventana' and 'Benicia' with a calyx that is distinctly larger than the corolla on primary fruit. The calyx for 'Fronteras' varies in position but frequently has a slight indent early in the season and is even with the fruit later in the season; each primary flower has 5-7 petals, similar to the comparison cultivars on average. The fruit shape for 'Fronteras' is consistent throughout the season, and is typically medium to long conic, with a tendency to be somewhat cylindrical and blunt. It is easily distinguished by fruit shape from 'Camarosa' (shortened and flattened conic), or 'Ventana' (medium symmetrical conic), and 'Benicia' (often flattened). Fruit size for 'Fronteras' is substantially larger than for the comparison cultivars. External fruit color for 'Fronteras' is similar to that for 'Camarosa', lighter than for 'Benicia', and darker than for 'Ventana'; internal color for 'Fronteras' is somewhat lighter than for the comparison cultivars (Table 3). Achenes vary from yellow to dark red, and are even with the fruit surface or slightly indented.

TABLE 3

Foliar and fruit color characteristics for 'Fronteras' and three comparison cultivars.

| | Cultivar | | | |
|---|---|---|---|---|
| Color Character | 'Camarosa' | 'Ventana' | 'Benicia | 'Fronteras' |
| Leaf color (CIELAB) Adaxial L* | | | | |
| mean | 38.3 | 39.2 | 35.0 | 38.3 |
| range | 37.3-39.8 | 36.0-41.1 | 33.3-36.4 | 34.8-41.1 |
| a* | | | | |
| mean | −12.2 | −14.3 | −11.7 | −13.0 |
| range | −9.5--15.5 | −12.9--16.7 | −10.3--13.5 | −11.3--15.6 |
| b* | | | | |
| mean | 16.9 | 20.6 | 16.9 | 18.7 |
| range | 13.3-19.9 | 17.3-24.8 | 13.1-21.7 | 13.8-22.6 |
| Munsell | 5 GY 5/5 | 2.5 GY 6/8 | 5 GY 5/6 | 5 GY 4/3 |
| Abaxial L* | | | | |
| mean | 52.5 | 53.2 | 48.5 | 48.9 |
| range | 51.3-54.6 | 51.8-54.6 | 41.7-52.3 | 40.2-51.2 |

TABLE 3-continued

Foliar and fruit color characteristics for 'Fronteras' and three comparison cultivars.

| | Cultivar | | | |
|---|---|---|---|---|
| Color Character | 'Camarosa' | 'Ventana' | 'Benicia | 'Fronteras' |
| a* | | | | |
| mean | −13.1 | −14.2 | −13.5 | −14.1 |
| range | −11.4--14.9 | −13.9--14.7 | −11.9--16.8 | −13.0 −15.1 |
| b* | | | | |
| mean | 20.5 | 21.7 | 20.0 | 21.4 |
| range | 18.9-22.4 | 20.3-23.3 | 17.9-21.9 | 20.0-21.9 |
| Munsell | 7.5 GY 8/7 | 10 GY 8/7 | 7.5 GY 5/7 | 10 GY 7/8 |
| Fruit color (CIELAB) External L* | | | | |
| mean | 38.6 | 38.1 | 36.0 | 36.9 |
| range | 34.7-42.7 | 37.6-39.0 | 34.2-37.5 | 35.5-37.3 |
| a* | | | | |
| mean | 34.4 | 33.4 | 31.2 | 37.3 |
| range | 33.6-36.2 | 29.4-38.7 | 26.6-36.3 | 35.1-39.9 |
| b* | | | | |
| mean | 22.5 | 19.2 | 14.2 | 19.2 |
| range | 18.8-29.3 | 17.8-21.1 | 10.6-17.3 | 16.7-19.0 |
| Munsell | 7.5 R 4/11 | 5 R 4/12 | 2.5 R 4/0 | 7.5 R 4/11 |
| Internal L* | | | | |
| mean | 50.2 | 48.6 | 44.0 | 55.7 |
| range | 46.6-53.3 | 46.2-52.3 | 40.8-47.0 | 50.4-60.4 |
| a* | | | | |
| mean | 30.8 | 28.9 | 30.9 | 20.9 |
| range | 25.6-35.4 | 23.5-33.0 | 27.8-33.6 | 18.1-25.9 |
| b* | | | | |
| mean | 30.1 | 31.3 | 27.5 | 25.4 |
| range | 28.0-32.0 | 30.6-32.5 | 24.6-28.8 | 19.6-30.7 |
| Munsell | 7.5 R 5/13 | 7.5 R 6/13 | 5 R 4/2 | 7.5 R 5/3 |
| Achene color Munsell | 2.5 Y 7/10 | 10 Y 8/11 | 5 R3/7 | 2.5 R 8/12 |

TABLE 4

Flower and fruit characters for 'Fronteras' and three comparison cultivars.

| | Cultivar | | | |
|---|---|---|---|---|
| Character | 'Camarosa' | 'Ventana' | 'Benicia | 'Fronteras' |
| Petal number | | | | |
| mean | 5.8 | 6.2 | 6.1 | 5.9 |
| range | 5-7 | 5-7 | 5-7 | 5-7 |
| Petal shape | | | | |
| apex | truncate to slightly obtuse | truncate to slightly obtuse | truncate to slightly obtuse | truncate to slightly obtuse |
| base | attenuate | attenuate | attenuate | attenuate |
| margin | entire | entire | entire | entire |
| Petal length (mm) | | | | |
| mean | 11.5 | 13.3 | 11.7 | 13.5 |
| range | 10-13 | 11-15 | 8-13 | 13-15 |

TABLE 4-continued

Flower and fruit characters for 'Fronteras' and three comparison cultivars.

| Character | Cultivar 'Camarosa' | 'Ventana' | 'Benicia' | 'Fronteras' |
|---|---|---|---|---|
| Petal width (mm) | | | | |
| mean | 12.0 | 14.6 | 14.4 | 12.6 |
| range | 10-14 | 13-16 | 8-13 | 8-14 |
| Flower position (relative to foliage) | most even some exposed | even to exposed | even to exposed | most even some interior |
| Calyx diam. (mm) | | | | |
| mean | 40.4 | 47.0 | 50.8 | 48.3 |
| range | 33-47 | 40-50 | 47-53 | 44-54 |
| Corolla diam. (mm) | | | | |
| mean | 26.1 | 39.0 | 39.6 | 31.3 |
| range | 23-31 | 35-45 | 39-41 | 29-38 |
| Sepal length (mm) | | | | |
| mean | 14.3 | 16.6 | 16.4 | 14.6 |
| range | 12-18 | 14-19 | 13-20 | 11-17 |
| Sepal width (mm) | | | | |
| mean | 8.3 | 8.4 | 8.4 | 9.3 |
| range | 7-10 | 7-10 | 7-10 | 7-11 |
| Sepal color (Munsell) | 5 GY 7/10 | 5 GY 5/5 | 10 GY 8/7 | 5 GY 5/6 |
| Pedicel length (mm) | | | | |
| mean | 155 | 115 | 183 | 125 |
| range | 130-180 | 90-140 | 150-210 | 90-170 |
| Pedicel diameter (mm) | | | | |
| mean | 2.7 | 3.5 | 3.7 | 4.7 |
| range | 2-4 | 3-4 | 3-5 | 4-6 |
| Pedicel color | 7.5 GY 8/7 | 5 GY 8/9 | 2.5 GY 8/9 | 7.5 GY 6/8 |
| Fruit shape | | | | |
| Fruit length (mm) | | | | |
| mean | 46.0 | 48.4 | 46.5 | 54.5 |
| range | 40-48 | 47-52 | 41-52 | 51-58 |
| Fruit width (mm) | | | | |
| mean | 37.4 | 42.6 | 42.4 | 46.7 |
| range | 33-46 | 40-46 | 36-46 | 42-54 |
| Length/width | | | | |
| ratio | 1.26 | 1.17 | 1.08 | 1.15 |
| range | 1.0-1.4 | 1.1-1.2 | 1.0-1.2 | 1.0-1.2 |
| subjective | Obovate-flat | Medium conic | Medium conic | Medium-long conic |
| Primary/secondary fruit comparison | | | | |
| size (subjective) | 50-70% | 55-75% | 55-65% | 60-80% |
| shape | similar shape, more conic | similar shape | similar shape | similar shape |

TABLE 4-continued

Flower and fruit characters for 'Fronteras' and three comparison cultivars.

| Character | Cultivar 'Camarosa' | 'Ventana' | 'Benicia' | 'Fronteras' |
|---|---|---|---|---|
| Extent/size of hollow core | small-absent | small | small-absent | small-absent |
| Calyx | | | | |
| position | indented-neck | indent-reflexed | even-indented | Indented-even |
| size relative to fruit | equal or less than fruit diameter | equal or less than fruit diameter | equal or greater than fruit diameter | equal or less than fruit diameter |
| Seed position | indented-extruded | mostly even | even-indented | indented-extruded |
| Adherence of Calyx to Fruit | weak | intermediate | weak | intermediate |

Flower and plant measurements obtained on April, 2012, fruit measurements May 10-20, 2012.

'Fronteras' has been tested under a variety of cultural regimes, and optimal performance is obtained when nursery treatments and nutritional programs similar to those for 'Camarosa', 'Ventana', and 'Benicia' are used. In general, plants of 'Fronteras' are greater in vigor than the comparison cultivars with very early season planting. 'Fronteras' retains excellent fruit quality in summer planting systems.

When treated with appropriate planting regimes, 'Fronteras' has substantially larger sized fruit and produces individual-plant yields greater than any of the comparison cultivars (Table 5). Commercial appearance ratings have also been substantially better than those for all of the comparison cultivars, especially in comparison with 'Camarosa'. Fruit for 'Fronteras' is similar in firmness to fruit from 'Ventana', less firm than the other comparison cultivars. Subjectively, 'Fronteras' has excellent flavor. The fruit will be exceptional for both fresh market and processing, and will be useful for home garden purposes.

TABLE 5

'Fronteras' and three comparison cultivars evaluated near Watsonville, CA in 2010-12. All plants for these trials were harvested from a commercial nursery near Macdoel, CA on October 15-16, and transplanted after 6-7 days supplemental storage. Fruit harvest was initiated in early April and continued through the last week of August. (52" 2-row beds, 17,300 plants/acre).

| Item | Yield (g/plant) | Appearance Score (5 = best) | Fruit Size (g/fruit) | Firmness |
|---|---|---|---|---|
| 'Camarosa' | 1,815 | 2.8 | 27.1 | 11.6 |
| 'Ventana' | 2,080 | 3.3 | 30.1 | 10.2 |
| 'Benicia' | 1,649 | 3.4 | 33.1 | 11.1 |
| 'Fronteras' | 2,793 | 4.2 | 35.1 | 11.1 |

What is claimed is:

1. A new and distinct cultivar of strawberry plant having the characteristics substantially as described and illustrated herein.

* * * * *